United States Patent
Kampfen et al.

(10) Patent No.: US 7,268,255 B2
(45) Date of Patent: Sep. 11, 2007

(54) PROCESS FOR THE PREPARATION OF N-SUBSTITUTED FORMAMIDES

(75) Inventors: Ulrich Kampfen, Brig (CH); Dario Veghini, Brig-Glis (CH); Dominique Roberge, Sierre (CH); Jared Randall, Smyma, NY (US)

(73) Assignee: Lonza AG, Basel (CH)

( * ) Notice: Subject to any disclaimer, the term of this patent is extended or adjusted under 35 U.S.C. 154(b) by 0 days.

(21) Appl. No.: 10/546,291

(22) PCT Filed: Feb. 19, 2004

(86) PCT No.: PCT/EP2004/001593

§ 371 (c)(1),
(2), (4) Date: Sep. 18, 2006

(87) PCT Pub. No.: WO2004/074234

PCT Pub. Date: Sep. 2, 2004

(65) Prior Publication Data

US 2007/0037985 A1    Feb. 15, 2007

Related U.S. Application Data

(60) Provisional application No. 60/448,123, filed on Feb. 20, 2003.

(51) Int. Cl.
C07C 233/03    (2006.01)
C07C 231/02    (2006.01)
C07D 235/04    (2006.01)

(52) U.S. Cl. .................................. 564/218; 548/304.7
(58) Field of Classification Search ............... 564/218; 548/304.7

See application file for complete search history.

(56) References Cited

OTHER PUBLICATIONS

Pratap et al, Tetrahedron Letters, vol. 42, (2001), 1983-1985.*
Hrvatin et al, Synlett, Sep. 1997, pp. 1069-1070.*

* cited by examiner

*Primary Examiner*—Shailendra Kumar
(74) *Attorney, Agent, or Firm*—Fisher, Christen & Sabol

(57) ABSTRACT

N-Aryl or N-heteroarylformamides are prepared by hydrogenating a corresponding nitroarene or nitroheteroarene with formic acid and/or ammonium formate as hydrogen donor and formylating agent in the presence of at least one noble metal-based hydrogenation catalyst and a vanadium or molybdenum compound as co-catalyst.

27 Claims, No Drawings

PROCESS FOR THE PREPARATION OF N-SUBSTITUTED FORMAMIDES

This is a 371 national stage application of International (PCT) Patent Application No. PCT/EP2004/001593, filed on Feb. 19, 2004, that has benefit of U.S. Provisional Application Ser. No. 60/448,123, filed on Feb. 20, 2003.

The invention relates to a process for the preparation of N-aryl- or N-heteroarylformamides from nitroarenes or nitroheteroarenes by reductive formylation.

N-Aryl- and N-heteroarylformamides are valuable intermediates for the synthesis of various compounds. They can, for example, be dehydrated to form isonitriles (U.S. Pat. No. 3,636,036). The formyl group can also act as an amino protective group which can be cleaved by treatment with strong acid. Other applications of N-aryl- and N-heteroarylformamides include their use as developers for thermal recording materials (JP-A-09-193553) or as additives for polymerization catalysts (U.S. Pat. No. 5,153,767).

Known methods for the production of N-Aryl- and N-heteroarylformamides are based on the reaction of the corresponding aryl- and heteroarylamines with formic acid. Common methods for she production of arylamines involve the reduction of the corresponding nitroarenes either by hydrogenation or with iron as reducing agent. WO-A-96/36597 discloses the hydrogenation of nitroarenes to arylamines with gaseous hydrogen using noble metal catalysts in the presence of minute amounts of vanadium compounds. In one example, the arylamine is acetylated in situ when sodium acetate is present in the reaction mixture. The use of pressurized (up to 20 bar) gaseous hydrogen and autoclaves is a disadvantage of that method.

An object of the present invention is to provide a simple one-step method for the production of N-aryl- and N-heteroarylformamides from the corresponding nitro compounds.

A further object of the present invention is to provide a one-step method for the production of benzimidazoles from arenes bearing nitro amino groups on adjacent ring carbon atoms. Substituted benzimidazoles are valuable intermediates in the synthesis of pharmaceutically active compounds.

It has been found that it is possible to produce N-aryl- or N-heteroarylformamides by hydrogenating corresponding nitroarenes or nitroheteroarenes with formic acid and/or ammonium formate as hydrogen donor and formylating agent in the presence of at least one noble metal-based hydrogenation catalyst and a vanadium or molybdenum compound as co-catalyst. A particular advantage of this method resides in the fact that it can he carried out at ambient pressure without using gaseous hydrogen.

The terms arene and aryl are here and hereinbelow to be understood as meaning all mono-, bi-and polycyclic aromatic hydrocarbons such as, for example, benzene, biphenyl, naphthalene, indane, indane, anthracene, phenanthrene, fluorene, pyrene and perylene and the monovalent radicals (such as phenyl, biphenylyl, naphthyl etc.) derived from the beforementioned hydrocarbons, respectively.

Accordingly, the terms heteroarene and heteroaryl are here and hereinbelow to be understood as meaning all mono-, bi- and polycyclic aromatic compounds containing at least one ring atom other than carbon, in particular nitrogen, oxygen or sulfur, and the monovalent radicals derived therefrom, respectively. Examples of heteroarenes are pyridine, pyrimidine, pyrazine, pyridazine, pyrrole, pyrazole, imidazole, furan, thiophene, thiazole, indole, isoindole, indolizine, quinoline, isoquinoline, quinoxaline, quinazoline, cinnoline, naphthyridine, carbazole, acridine and phenazine.

The term, noble metal is here and hereinbelow to be understood as meaning, in particular, the metals known as platinum metals, i.e., rhodium, rutheninum, palladium, osmium, iridium and platinum.

In a preferred embodiment of the present invention, the N-aryl- or N-heteroarylformamide has the formula

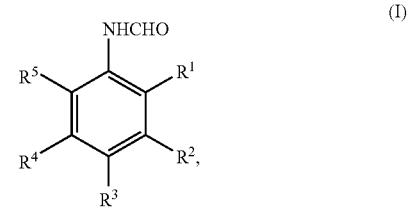

(I)

wherein the substituents $R^1$ and $R^5$ are independently selected from the group consisting of hydrogen, halogen, $C_{1-6}$-alkyl, $C_{1-6}$-alkoxy, cyano, carboxy, di($C_{1-6}$-alkyl)amino, $C_{1-6}$-alkoxycarbonyl, and aryl;

$R^2$ through $R^4$ are independently selected from the group consisting of hydrogen, halogen, $C_{1-6}$-alkyl, $C_{1-6}$-alkoxy, cyano, carboxy, di($C_{1-6}$-alkyl)amino, $C_{1-6}$-alkoxycarbonyl, aryl and —NHCHO;

and/or two or more of $R^1$ through $R^5$ together with the depicted phenyl moiety form a bicyclic or polycyclic fused carbocyclic or heterocyclic ring system;

and the corresponding nitroarene or nitroheteroarene has the formula

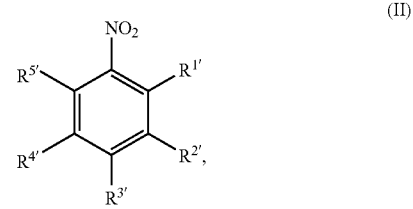

(II)

wherein each of $R^{1'}$ through $R^{5'}$ has the same meaning as the corresponding substituent $R^1$, $R^2$, $R^3$, $R^4$ and $R^5$ in formula (I) or, if said corresponding substituent is —NHCHO, is —$NO_2$ or —$NH_2$. Here and hereinbelow, the term $C_{1-6}$-alkyl is to be understood as meaning any linear or branched alkyl group having one to six carbon atoms, such as, for example, methyl, ethyl, propyl, isopropyl, butyl, isobutyl, sec-butyl, tert-butyl, pentyl, isopentyl, tert-pentyl, neopentyl, hexyl and the like. Consequently, the terms $C_{1-6}$-alkoxy, $C_{1-6}$-alkoxycarbonyl and di($C_{1-6}$-alkyl)amino are to be understood as meaning any moiety composed of the beforementioned $C_{1-6}$-alkyl groups and oxygen, carbonyloxy (—OC(=O)—) or nitrogen, respectively.

Bicyclic and polycyclic fused carbocyclic and heterocyclic ring systems containing a phenyl moiety are, for example, napthalene, indane, tetrahydronaphthalene, fluorene, anthracene, phenanthrene, acenaphthene, pyrene and perylene as carbocyclic and indole, benzimidazole, thionaphthene, quinoline, quinoxaline, chroman, chromene, carbazole and acridine as heterocyclic systems.

In another preferred embodiment of the present invention, the N-aryl- or N-heteroarylformamide formed contains an amino group on a carbon atom adjacent to that bearing the nitro group which reacts in situ with the formamide moiety to form an imidazole ring, thus forming a benzimidazole system. If, for example, o-nitroaniline is employed as starting material, benzimidazole will be the product.

In a more preferred embodiment, the N-heteroarylformamide ultimately formed is a benzimidazole which has the formula

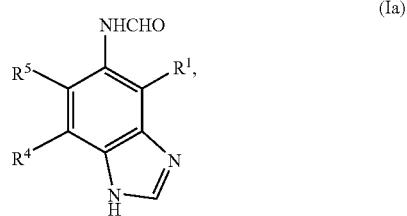

(Ia)

wherein the substituents $R^1$, $R^4$ and $R^5$ are as defined above, and the corresponding nitroarene has the formula

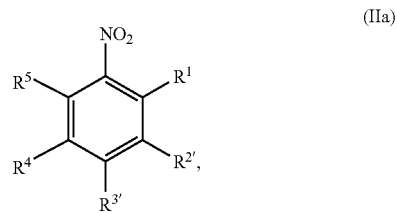

(IIa)

wherein one of $R^{2'}$ and $R^{3'}$ is —$NO_2$ and the other is —$NH_2$; and $R^1$, $R^4$ and $R^5$ are as defined above for formula (Ia).

Especially preferred nitroarenes (IIa) are those wherein $R^2$ is —$NO_2$, and $R^{3'}$ is —$NH_2$, in particular those wherein $R^1$ is methyl and $R^4$ is cyano. The formylamino group of the corresponding benzimidazoles (Ia) can be hydrolyzed to yield the corresponding amines which are intermediates in the synthesis of α-adrenoceptor agonists (WO-A-99/26942).

The benzimidazoles (Ia) may occur in either of two tautomeric forms (1H and 3H form) or as a mixture of both. For the sake of simplicity, only one form is depicted here.

Preferably, the noble-metal based hydrogenation catalyst is platinum, in particular platinum on a support such as charcoal.

More preferably, the platinum is "poisoned", in particular sulfided.

In oder to obtain high yields of the desired formamides or benzimidazoles with low formation of byproducts or incompletely reduced product such as hydroxylamines or O-formylhydroxylamines, it is essential to add co-catalysts such as vanadium or molybdenum compounds. Preferably, the vanadium or molybdenum compound is selected from the group consisting of vanadium (v) oxide ($V_2O_5$), ammonium metavanadate ($NH_4VO_3$) and molybdates such as sodium molybdate ($Na_2MoO_4$).

Preferably, the hydrogenation is carried out at ambient pressure.

The present invention will be concretely illustrated with reference to the examples. It is to be noted, however, that the present invention is not limited to them.

EXAMPLE 1

Formanilide (N-phenylformamide)

Nitrobenzene (12.31 g, 100 mmol), formic acid (80%; 278 mL, 328.0 g), a sulfided platinum catalyst (5% Pt on charcoal, Engelhard No. 43045, lot No. 08554; dry weight 1.55 g) and vanadium(v) oxide (57 mg) were charged under argon in a double-walled 0.3 L stirring vessel with temperature control. The argon flow was stopped and the slurry was heated to 91-94° C. for 2 h. HPLC analysis of the reaction mixture indicated a 79.9% yield of formanilide, accompanied by 18.3% of aniline.

EXAMPLE 2 (COMPARATIVE EXAMPLE)

Formanilide (N-phenylformamide)

The procedure of Example 1 was repeated without vanadium(v) oxide. After 3 h reaction time the yield of formanilide was 55% and 30.6% of N-formyloxyaniline and 10.2% of aniline were formed as byproducts.

EXAMPLE 3

1-Chloro-2,4-formylamino)benzene

The procedure of Example 1 repeated using 1-chloro-2, 4-dinitrobenzene (100 mmol, 20.26 g) as starting compound. The reaction temperature was 91-95° C. and the yield of 1-chloro-2,4-bis(formylamino)benzene was 77.0%. The partially reduced compound 1-chloro-2(4)-formylamino-4(2)-nitrobenzene was formed in 20.5% yield.

EXAMPLE 4

1-Chloro-2,4-bis(formylamino)benzene

1-Chloro-2,4-dinitrobenzene (4 mmol, 0.81 g), aqueous formic acid (80%; 11 mL, 13 g), sulfided platinum catalyst (5% Pt on charcoal, Engelhard No. 43045, lot No. 08554; dry weight 62 mg) and sodium molybdate dihydrate (2.3 mg) were charged under argon in a small stirring vessel. The argon flow was stopped and the slurry was heated to 90-95° C. for 2.5 h giving 1-chloro-2,4-bis(formylamino)benzene in 76.1% yield. The partially reduced compound 1-chloro-2 (4)-formylamino-4(2)-nitrobenzene was formed in 20.5% yield.

EXAMPLE 5

1-Chloro-2,4bis(formylamino)benzene

The procedure of Example 4 was repeated using ammonium metavanadate (2 mg) instead of sodium molybdate dihydrate. After 2.5 h reaction time at 90-95° C. the yield of 1-chloro-2,4-bis(formylamino)benzene was 77.2%. The partially reduced compound 1-chloro-2(4)-formylamino-4(2)-nitrobenzene was formed in 20.5% yield.

EXAMPLE 6

1-Chloro-2,4-bis(formylamino)benzene

1-Chloro-2,4-dinitrobenzene (4 mmol, 0.81 g), ammonium formate (ca. 40 mmol, 2.6 g), sulfided platinum catalyst (5% Pt on charcoal, Engelhard No. 43045, lot No.

08554; dry weight 62 mg) and acetonitrile (11 mL) were charged under argon in a small stirring vessel. The argon flow was stopped and the slurry was heated to 80° C. for 2.5 h giving 1-chloro-2,4-bis(formylamino)benzene in 88.5% yield.

EXAMPLE 7

1-Chloro-2,4-bis(formylamino)benzene

The procedure of Example 6 was repeated with addition of vanadium(v) oxide (2.3 mg). After 2.5 h reaction time at 80° C. the yield of 1-chloro-2,4-bis(formylamino)benzene was 95.7%.

EXAMPLE 8

1-Formylamino-4-methylbenzene (p-formotoluidide)

The procedure of Example 7 was repeated using p-nitrotoluene (4 mmol, 0.55 g) as starting compound. The reaction temperature was 80° C. and after 2.5 h reaction time the yield of 1-formylamino-4-methylbenzene was 87.9%. 4-Methylaniline (11.2%) was formed as byproduct.

EXAMPLE 9

1,3-Bis(formylamino)-2-methylbenzene

The procedure of Example 4 was repeated with 2,6-dinitrotoluene (4 mmol, 0.81 g) as starting material. The combined yield of 1,3-bis(formylamino) 2-methylbenzene and 1-amino-3-formylamino-2-methylbenzene was 97.2%.

EXAMPLE 10 (COMPARATIVE EXAMPLE)

1,3-Bis(formylamino)-2-methylbenzene

The procedure of Example 9 was repeated without sodium molybdate. The combined yield of 1,3-bis(formylamino)-2-methylbenzene and 1-amino-3-formylamino-2-methylbenzene was 79.0%.

EXAMPLE 11

1,3-Bis(formylamino)-2-methylbenzene

The procedure of Example 9 was repeated with addition of vanadium(v) oxide (2.3 mg) instead of sodium molybdate dihydrate. The combined yield of 1,3-bis(formylamino)-2-methylbenzene and 1-amino-3-formylamino-2-methylbenzene was 98.1%.

EXAMPLE 12

2-Amino-4-methyl-3,5-dinitrobenzonitrile

A solution of 4-methyl-3,5-dinitrobenzonitrile (10.5 kg; preparation see U.S. Pat. No. 3,162,675), 4-amino-4H-1,2,4-triazole (17.0 kg) and dimethyl sulfoxide (68.6 kg) was dosed into a mixture of lithium tert-butoxide (12.2 kg) and dimethyl sulfoxide (106.6 kg) over about 50 min, while maintaining the temperature of each solution at 20-25° C. After aging at 20-25° C. for about 2 h, acetic acid (8.9 kg) was dosed into the reaction mixture at about 20° C. over about 10 min. The product was crystallized by dosing water (158 L) into the reaction mixture over about 1.5 h at about 20° C. The product slurry was cooled to 10-15° C. and held at this temperature for about 45 min. The resultant slurry was filtered, and washed with water (106 L). The wet cake obtained was dried in a vacuum tray dryer at about 50° C. and 30 Torr to provide 2-amino-4-methyl-3,5-dinitrobenzonitrile as an orange-brown solid.

Yield: 9.8 kg (87%).

EXAMPLE 13

5-Formylamino-4-methyl-1H-benzimidazole-7-carbonitrile[N-(7-Cyano-4-methyl-1H-benzoimidazol- A double-walled 1 L stirring vessel with temperature control was charged under argon with 2-amino-4-methyl-3,5-dinitrobenzonitrile (IIa, $R^1$=Me, $R^2$=NO$_2$, $R^{3'}$=NH$_2$ $R^4$=CN, $R^5$=H; 22.2 g, 100 mmol), formic acid (80% in water; 328.0 g), a sulfided platinum catalyst (5% Pt on charcoal, 57.8% moisture content, obtained from Engelhard Italy, Sample Code 43045; 2.44 g) and a platinum/vanadium catalyst (5% Pt+1% V on charcoal, moisture content 61.74%, Degussa CF 1082 XBA/W; 1.22 g). The argon flow was stopped and the slurry was heated to 90° C. within 50 min while a development of carbon dioxide commenced. The reaction mixture was kept for another 2 h at 90-93° C. under vigorous gas development while the reaction progress was monitored by HPLC. After the reaction was complete the mixture was cooled to 25° C. and the black suspension was filtered through a 1 cm layer of Celite® which was subsequently washed with 80% aqueous formic acid (50 g). The bright orange filtrate was concentrated to ca. 150 g in a rotary evaporator at 45° C./30 mbar. Methanol (118.0 g, 150 mL) was added and after 15 min at 45° C. the mixture was cooled to 0° C. within ½ h and stirred for another hour. The precipitated product was filtered off and the product filter cake was washed with methanol (58.2 g, 74 mL). The thus obtained product (21.7 g) was dried for 15 h at 45° C./25 mbar.

Yield: 15.3 g (75.9%, Assay (HPLC): 99.3%.

m.p. >310° C.

According to NMR data the product was a mixture of conformers and/or tautomers. In the following, only the chemical shifts of the dominating isomer (83%) are given.

$^1$H NMR (DMSO-d$_6$): δ=13.2 (br. s, 1H), 9.87 (br. s, 1H), 8.47 (s, 1H), 8.35 (d,j=1.8Hz,1H), 7.91 (s, 1H), 2.48 (s, 2H).

$^{13}$C NMR (DMSO-d$_6$): δ=160.1, 144.6, 140.5, 134.0, 129.9, 123.0, 121.6, 117.1, 97.8, 13.1.

EXAMPLE 14

5-Amino-4-methyl-1H-benzimidazole-7-carbonitrile

A mixture of 5-(formylamino)-4-methyl-1H-benzimidazole-7-carbonitrile (4.8 kg), water (46 L) and concentrated hydrochloric acid (17.8 kg) was agitated at about 80° C. for about 1½ h. After the mixture was cooled to about 25° C., a solution of 50% aqueous sodium hydroxide (17.1 kg) and water (64 L) was added. The mixture was cooled to about 25° C. over about 15 min. The mixtures was then filtered and the product was washed with water (50 L). The product was dried in a vacuum tray dryer at 45-50° C. and ca. 40 Torr.

Yield: 3.8 kg (94%).

EXAMPLE 15

1-Formylamino-2-methoxybenzene (o-formoanisidide)

The procedure of Example 4 was repeated using o-nitroanisole (4 mmol, 0.55 g) as starting material and vanadium(v) oxide (2.3 mg) instead of sodium molybdate dihydrate. After 2.5 h at 90-95° C. a yield of 24.8% of o-formoanisidide was obtained. o-Anisidine (62.8%) was found to be the main product.

EXAMPLE 16

1-Formylaminonaphthalene

The procedure of Example 4 was repeated using 1-nitronaphthalene (4 mmol, 0.61 g) as starting material and vanadium(v) oxide (2.3 mg) instead of sodium molybdate dihydrate. After 2.5 h at 90-95° C. a yield of 22.3% of 1-formylaminonaphthalene was obtained. α-Naphthylamine (60.8%) was found to be the main product.

The invention claimed is:

1. A method of making an N-aryl- or N-heteroarylformamide comprising hydrogenating a corresponding nitroarene or nitroheteroarene with formic acid and/or ammonium formate as hydrogen donor and formylating agent in the presence of at least one noble metal-based hydrogenation catalyst and a vanadium or molybdenum compound as co-catalyst.

2. The method of claim 1 wherein the N-aryl-or N-heteroarylformamide has formula:

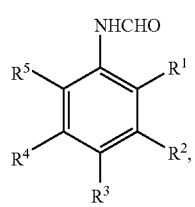

(I)

wherein the substituents $R^1$ and $R^2$ are independently selected from the group consisting of hydrogen, halogen, $C_{1-6}$-alkyl, $C_{1-3}$-alkoxy, oyano, carboxy, di($C_{1-6}$-alkyl)amino, $C_{1-6}$-alkoxycarbonyl, and aryl;

$R^2$ through $R^4$ are independently selected from the group consisting of hydrogen, halogen, $C_{1-6}$-alkyl, $C_{1-6}$-alkoxy, cyano, carboxy, di($C_{1-5}$-alkyl)amino, $C_{1-6}$-alkoxycarbonyl, aryl and NHCHO;

and/or two or more of $R^1$ through $R^5$ together with the depicted phenyl moiety form a bicyclic or polycyclic fused carbocyclic or heterocyclic ring system;

and the corresponding nitroarene or nitroheteroarene has formula:

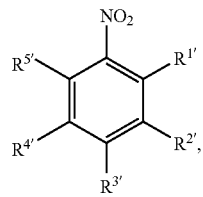

(II)

wherein each of $R^{1'}$ through $R^{5'}$ has the same meaning as the corresponding substituent $R^1$, $R^2$, $R^3$, $R^4$ and $R^5$ in formula (I) or, if said corresponding substituent is —NHCHO, is —NO$_2$ or —NH$_2$.

3. The method of claim 1 wherein the N-aryl- or N-heteroarylformamide formed contains an amino group which reacts in situ with the formamide moiety to form an imidazole ring.

4. The method of claim 3 wherein the N-heteroarylformamide has formula:

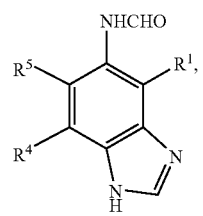

(Ia)

wherein the substituents $R^1$, $R^4$ and $R^5$ are as defined in claim 2, and the corresponding nitroarene has formula:

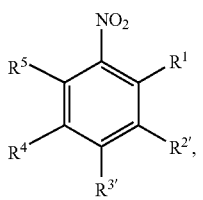

(IIa)

wherein one of $R^2$ and $R^3$ is —NO$_2$ and the other is —NH$_2$; and $R^1$, $R^4$ and $R^5$ are as defined above for formula (Ia).

5. The method of claim 4 wherein $R^2$ is —NO$_2$ and $R^3$ is —NH$_2$.

6. The method of claim 5 wherein $R^1$ is methyl and $R^4$ is cyano.

7. The method of claim 6 wherein the noble metal is platinum.

8. The method of claim 7 wherein the noble metal-based hydrogenation catalyst is platinum supported on charcoal.

9. The method of claim 8 wherein the platinum is sulfided.

10. The method of claim 9 wherein the vanadium or molybdenum compound is selected from the group consisting of vanadium(V) oxide, ammonium metavanadate and sodium molybdate.

11. The method of claim 10 wherein the hydrogenation is carried out at ambient pressure.

12. The method of claim 7 wherein the platinum is sulfided.

13. The method of claim 1 wherein the N-heteroarylformamide has formula:

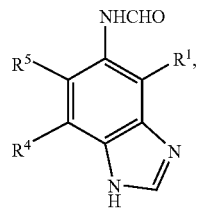

(Ia)

wherein the substituents $R^1$ and $R^5$ are independently selected from the group consisting of hydrogen, halogen, $C_{1-6}$-alkyl, $C_{1-3}$-alkoxy, cyano, carboxy, di($C_{1-6}$-alkyl)amino, $C_{1-6}$-alkoxycarbonyl, and aryl;

$R^4$ is independently selected from the group consisting of hydrogen, halogen, $C_{1-6}$ alkyl, $C_{1-3}$-alkoxy, cyano, carboxy, di($C_{1-6}$-alkyl)amino, $C_{1-6}$-alkoxycarbonyl, aryl and —NHCHO;

and the corresponding nitroarene has formula:

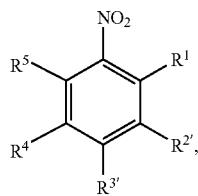

(IIa)

wherein one of $R^{2'}$ and $R^{3'}$ is —NO$_2$ and the other is —NH$_2$; and $R^1$, $R^4$ and $R^5$ are as defined above for formula (Ia).

14. The method of claim 13 wherein $R^{2'}$ is —NO$_2$ and $R^{3'}$ is —NH$_2$.

15. The method of claim 14 wherein $R^1$ is methyl and $R^4$ is cyano.

16. The method of claim 13 wherein the noble metal is platinum.

17. The method of claim 16 wherein the noble metal-based hydrogenation catalyst is platinum supported on charcoal.

18. The method of claim 16 wherein the platinum is sulfided.

19. The method of claim 17 wherein the platinum is sulfided.

20. The method of claim 13 wherein the vanadium or molybdenum compound is selected from the group consisting of vanadium(V) oxide, ammonium metavanadate and sodium molybdate.

21. The method of claim 1 wherein the hydrogenation is carried out at ambient pressure.

22. The method of claim 1 wherein the noble metal is platinum.

23. The method of claim 22 wherein the noble metal-based hydrogenation catalyst is platinum supported on charcoal.

24. The method of claim 23 wherein the platinum is sulfided.

25. The method of claim 22 wherein the platinum is sulfided.

26. The method of claim 1 wherein the vanadium or molybdenum compound is selected from the group consisting of vanadium(V) oxide, ammonium metavanadate and sodium molybdate.

27. The method of claim 26 wherein the hydrogenation is carried out at ambient pressure.

* * * * *